(12) United States Patent
Zhou

(10) Patent No.: US 7,569,046 B2
(45) Date of Patent: Aug. 4, 2009

(54) GUIDE-IN-GUIDE CATHETER SYSTEM

(75) Inventor: Pu Zhou, Plymouth, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 10/026,517

(22) Filed: Dec. 27, 2001

(65) Prior Publication Data

US 2003/0125712 A1    Jul. 3, 2003

(51) Int. Cl.
*A61M 25/00* (2006.01)

(52) U.S. Cl. .................. 604/530; 604/523; 604/524; 604/525; 604/531; 604/532; 604/95.05

(58) Field of Classification Search ............. 604/264, 604/158, 175, 523–532, 103.06, 529, 202, 604/164.11, 43, 500, 101.03, 506–510, 95.03–95.05, 604/8, 95.01; 606/41, 49, 50
See application file for complete search history.

(56) References Cited

U.S. PATENT DOCUMENTS

| | | | | |
|---|---|---|---|---|
| 4,050,466 A | | 9/1977 | Koerbacher | |
| 4,568,338 A | * | 2/1986 | Todd | 604/530 |
| 4,740,195 A | * | 4/1988 | Lanciano | 604/533 |
| 4,817,613 A | * | 4/1989 | Jaraczewski et al. | 600/435 |
| 5,085,649 A | * | 2/1992 | Flynn | 604/524 |
| 5,163,431 A | * | 11/1992 | Griep | 600/435 |
| 5,176,664 A | * | 1/1993 | Weisman | 604/317 |
| 5,222,949 A | * | 6/1993 | Kaldany | 604/524 |
| 5,322,521 A | * | 6/1994 | Wilk | 604/317 |
| 5,425,723 A | * | 6/1995 | Wang | 604/523 |
| 5,445,624 A | * | 8/1995 | Jimenez | 604/525 |
| 5,531,685 A | * | 7/1996 | Hemmer et al. | 604/95.05 |
| 5,554,114 A | * | 9/1996 | Wallace et al. | 604/508 |
| 5,569,218 A | * | 10/1996 | Berg | 604/525 |
| 5,599,325 A | * | 2/1997 | Ju et al. | 604/524 |
| 5,662,621 A | * | 9/1997 | Lafontaine | 604/528 |
| 5,676,659 A | * | 10/1997 | McGurk | 604/527 |
| 5,681,274 A | * | 10/1997 | Perkins et al. | 604/8 |
| 5,718,678 A | * | 2/1998 | Fleming, III | 604/43 |
| 5,817,072 A | * | 10/1998 | Lampropoulos et al. | 604/264 |
| 5,897,537 A | * | 4/1999 | Berg et al. | 604/525 |

(Continued)

FOREIGN PATENT DOCUMENTS

JP     08-057035 A     3/1996

(Continued)

*Primary Examiner*—Kevin C Sirmons
*Assistant Examiner*—Laura C Schell
(74) *Attorney, Agent, or Firm*—Crompton, Seager & Tufte, LLC

(57) ABSTRACT

A multiple catheter system is described. In one embodiment a medical catheter system includes a first catheter having an entrance orifice, an exit orifice, a channel connecting the entrance orifice and the exit orifice, and a wall surrounding the channel. In this embodiment the hardness of the wall surrounding the channel decreases in in hardness, increases in hardness and then decreases in hardness again, when considered from an initial reference point at the entrance orifice and traveling towards the exit orifice. Another medical catheter system includes a first catheter having an entrance orifice, an exit orifice, a channel linking the entrance orifice and the exit orifice, and a first wall surrounding the channel wherein the first wall has a bendable curve memory portion.

7 Claims, 6 Drawing Sheets

U.S. PATENT DOCUMENTS

| | | | |
|---|---|---|---|
| 5,911,715 A * | 6/1999 | Berg et al. | 604/525 |
| 6,036,682 A * | 3/2000 | Lange et al. | 604/529 |
| 6,093,177 A | 7/2000 | Javier, Jr. et al. | |
| 6,240,231 B1 * | 5/2001 | Ferrera et al. | 385/115 |
| 6,280,434 B1 * | 8/2001 | Kinoshita et al. | 604/530 |
| 6,295,990 B1 * | 10/2001 | Lewis et al. | 128/898 |
| 6,511,462 B1 * | 1/2003 | Itou et al. | 604/264 |
| 6,524,303 B1 * | 2/2003 | Garibaldi | 604/525 |
| 6,591,472 B1 * | 7/2003 | Noone et al. | 29/417 |
| 6,622,367 B1 * | 9/2003 | Bolduc et al. | 29/447 |
| 6,623,449 B2 * | 9/2003 | Paskar | 604/95.04 |
| 6,780,175 B1 * | 8/2004 | Sachdeva et al. | 604/531 |
| 6,858,024 B1 * | 2/2005 | Berg et al. | 604/525 |
| 2001/0047164 A1 * | 11/2001 | Teague et al. | |
| 2002/0077654 A1 | 6/2002 | Javier, Jr. et al. | |
| 2003/0023230 A1 | 1/2003 | Lews et al. | |

FOREIGN PATENT DOCUMENTS

| | | |
|---|---|---|
| JP | 09-140800 A | 6/1997 |
| WO | WO 00/69323 | 11/2000 |

* cited by examiner

GUIDE-IN-GUIDE CATHETER SYSTEM

FIELD OF THE INVENTION

The present invention regards catheter systems. More specifically, the present invention regards medical catheters that may surround one another when used to perform or complete medical procedures.

BACKGROUND

Intraluminal procedures are regularly carried out during the practice of contemporary medicine. These procedures may be completed within existing lumens of the body as well as in areas of the body that are not readily accessible through a lumen, in which case a temporary lumen may need to be inserted into the body to perform the procedure.

Intraluminal procedures may be performed to achieve numerous and various goals and objectives. These can include delivering therapeutic to a target site, analyzing and sampling tissue deep within the body, and performing surgical procedures. When performing any of these procedures a medical practitioner may first insert a working channel into the body and may then steer a second catheter through it to reach the target area. Upon reaching the target area, a third catheter may then be inserted into the second catheter, this time to perform the desired procedure. When, for example, the target area is within the heart, the outer catheter may be an LVS catheter while the second catheter may be a steerable catheter and the third catheter may be an injection catheter for delivering the therapeutic sought to be injected. Comparatively, when the target area is not accessible via a lumen, the outer catheter may be a rigid endoscope that is inserted into the body through an incision in the skin of the patient. Like the earlier described procedure, in this case as well, the second and third catheters may, then, be snaked into the endoscope to perform the procedure.

SUMMARY OF THE INVENTION

A multiple catheter system is described. In one embodiment a medical catheter system includes a first catheter having an entrance orifice, an exit orifice, a channel connecting the entrance orifice and the exit orifice, and a wall surrounding the channel. In this embodiment the hardness of the wall surrounding the channel decreases in hardness, increases in hardness and then decreases in hardness again, when considered from an initial reference point at the entrance orifice and traveling towards the exit orifice.

In another embodiment a medical catheter system includes a first catheter having an entrance orifice, an exit orifice, a channel linking the entrance orifice and the exit orifice, and a first wall surrounding the channel, the first wall having a bendable curve memory portion.

In yet another embodiment a medical catheter system includes a first catheter having an inner layer and an outer layer, the inner layer having a first hardness and the outer layer having a second hardness, the first hardness being harder than the second hardness.

DETAILED DESCRIPTION

Figure 1:
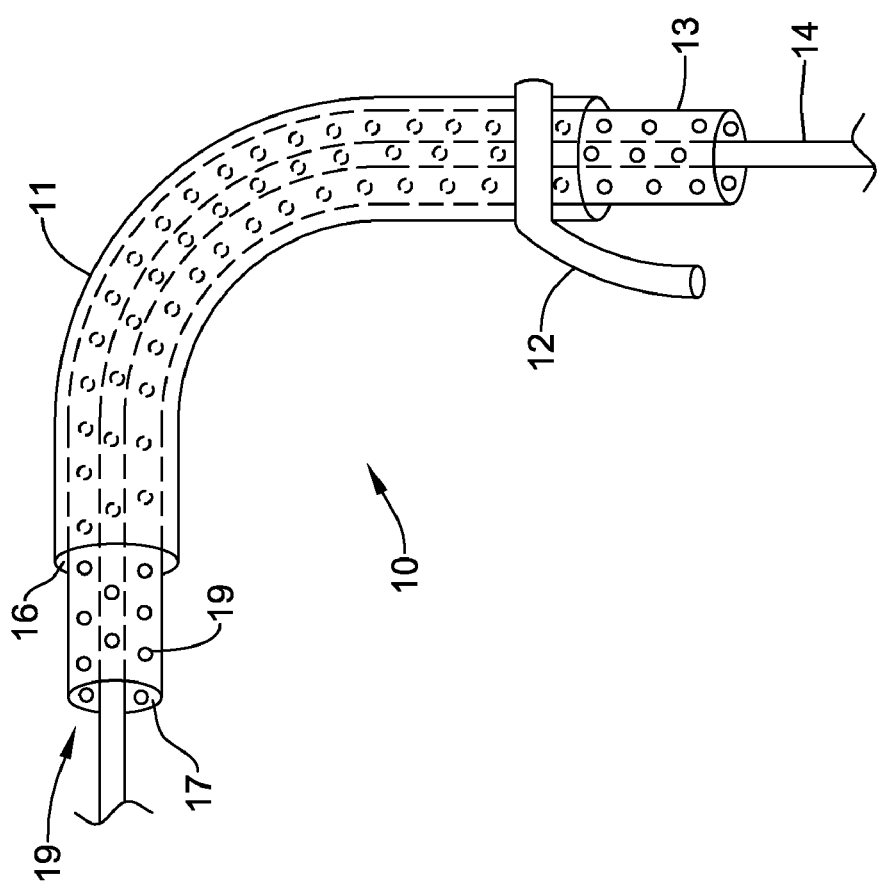
FIG. 1 is a side perspective view of a guide-in-guide catheter system in accord with one embodiment of the present invention.

FIG. 1 is a side perspective view of a guide-in-guide catheter system in accordance with an embodiment of the present invention. In FIG. 1, an outer catheter 11 is fluidly coupled to a flushing line 12. This outer catheter 11 has an inner duct or channel 16 that, as can be seen, contains a middle catheter 13. This middle catheter 13, a steerable catheter in this embodiment, has an inner duct or channel 17 and contains a plurality of flushing orifices 15 that are sized to allow fluid to pass through them. Located within the inner channel 17 of the middle catheter 13 is an inner catheter 14, which may be an injection catheter. This inner catheter 14 may be used to perform numerous procedures including therapeutic delivery and tissue sampling.

In use, the guide-in-guide catheter system 10 of FIG. 1 may be employed to access various portions and locations of different target sites within the body. It may be used by first positioning the outer catheter 11 near an area to be accessed and then by guiding the middle catheter 13 through the inner channel 16 of the outer catheter 11 until the distal end of the middle catheter 13 reaches an area near the target site. Then, once the target site becomes accessible via the inner channel 17 of the middle catheter 13, the inner catheter 14 may be inserted into the middle catheter 13 with its distal tip (which is not shown in FIG. 1) being positioned at the target site. Once the injection catheter 14 is appropriately positioned, the practitioner performing these steps may then complete a number of desirable medical procedures. These procedures could include delivering therapeutic, removing unwanted polyps, sampling malignant tissue, and freezing the target area; other steps, in addition to these, may also be performed as well.

By using this guide-in-guide system 10, target areas previously inaccessible through endoscopic or other intra-luminal procedures, may, now, be readily accessed via this system. For example, the outer catheter 11, in this embodiment an LVS catheter, may, first, be inserted into the left ventricle of the heart, then, once inserted, the middle catheter 13 may be steered through it such that its distal end 19 is positioned in the left ventricle of the heart. At this point the inner catheter 14 may then be snaked through the inner channel 17 of the steering guide catheter 13 until it reaches a target area within the left ventricle. Upon reaching the target area a medical procedure may be performed.

In another embodiment, the inner catheter 14 may not have any steering capabilities and, thus, it must rely upon the proper positioning of the middle catheter 13 in order to locate and access the target tissue. Alternatively, in addition to the steering capabilities of the middle catheter 13, the inner catheter 14 may also have some steering capabilities so that it may be further maneuvered after it emerges from the distal end 19 of the middle catheter 13 during the medical procedure being performed.

In each of these embodiments, as well as in others, a flushing fluid may be used to flush the target area and to flush the inner channels 16 and 17 of the catheters. In the embodiment of FIG. 1, a flushing line 12 may be fluidly connected to a pump (which is not shown) that can be used to pump flushing fluid into the proximal end of the outer catheter 11. Once the flushing operation has begun, due to the flushing orifices 15 in the middle catheter, flushing fluid may pass through the inner channel 16 of the outer catheter 11 to the surface of the middle catheter 13 and then into the inner channel 17 of the middle catheter 13 through flushing orifices 15. Consequently, through this arrangement, as described below in other embodiments, these flushing orifices 15 may provide a mechanism by which only a single flushing line may be used to flush more than one catheter (during the performance of a medical procedure).

Figure 2:
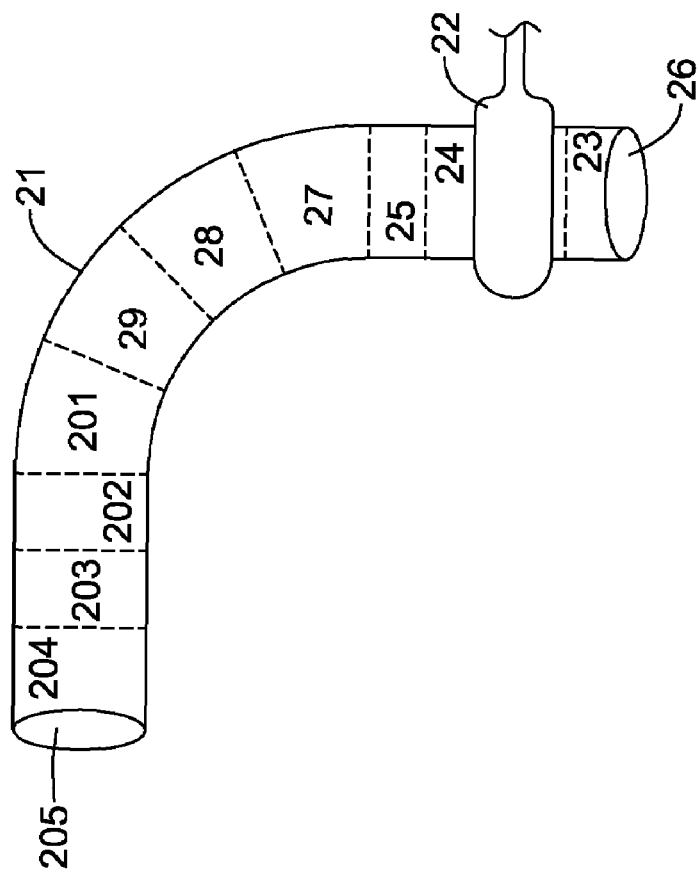
FIG. 2 is a side perspective view of an LVS catheter in accord with another embodiment of the present invention.

FIG. 2 is a side perspective view of an LVS catheter 21 in accordance with an alternative embodiment of the present invention. Visible in FIG. 2 are the various sections 23, 24, 25, 27, 28, 29, 209, 202, 203 and 204 of the LVS catheter 21. These sections differ in hardness from one another with hardnesses ranging from 30D (durameter) to 82D (durameter). Also visible in FIG. 2 is a flushing line 22 coupled to the LVS catheter 21 and entrance and exit orifices 26 and 205.

In this embodiment, the hardness of section 23 may be 74D, while the hardness of section 24 may be 63D and the hardness of section 25 may be 65D. Comparatively, the hardnesses of sections 27, 28, and 29 may respectively be 70D, 68D, and 64D, and the hardnesses of sections 201 through 204 may be 40D, 38D, 36D, and 30D, respectively. Thus, when traveling from the entrance orifice to the exit orifice, the hardness of the LVS catheter decreases, then increases, then decreases again.

It is preferable that the hardness of the material near the exit orifice of the LVS catheter be somewhat flexible so that when the LVS catheter is inserted into the left ventricle of the heart it will be less likely that the entering portion will do damage to it. Moreover, while the sections of the LVS catheter in FIG. 2 are defined and rather large in relation to the overall size of the LVS catheter, these sections may be smaller and less clearly defined in other embodiments. In each of these cases, though, it is preferable that the hardness of the catheter increases near both the distal most bend as well as at any other bend in the catheter and that it decreases near the exit orifice of the catheter.

In an alternative embodiment, the sections may not be as clearly defined with the hardness simply decreasing and then increasing and then decreasing again, in a more continuous fashion, when traveling from the entrance orifice 26 to the exit orifice 205. It is preferable, in this embodiment, that the curved section, (sections 27 28, 29 and 201) be generally harder than the areas directly surrounding it, (sections 202, 203, 204 and sections 25 and 24). An advantage of this configuration is that when a steerable catheter is guided through the LVS catheter 21, the curved portion, sections 27, 28, 29 and 201, will be better suited to re-direct the steering catheter as it is urged through the LVS catheter 21.

Furthermore, while a single turn is shown in this figure, other configurations for the LVS catheter are also plausible. For example, a 'U' catheter may be used for some applications while an 'S' catheter may be used for others. In a preferred embodiment of the LVS catheter 21 of FIG. 2, the outside diameter of the LVS catheter may be 7 French (0.092").

However, other sizes and cross-sectional configurations may also be used. This would include oval, stellate, rectangular or semi-circular cross-sections. Moreover, while sections 27, 28, 29 and 201 are described as having different hardness ratings, these four sections may have the same hardness rating in a different embodiment.

Figure 3:
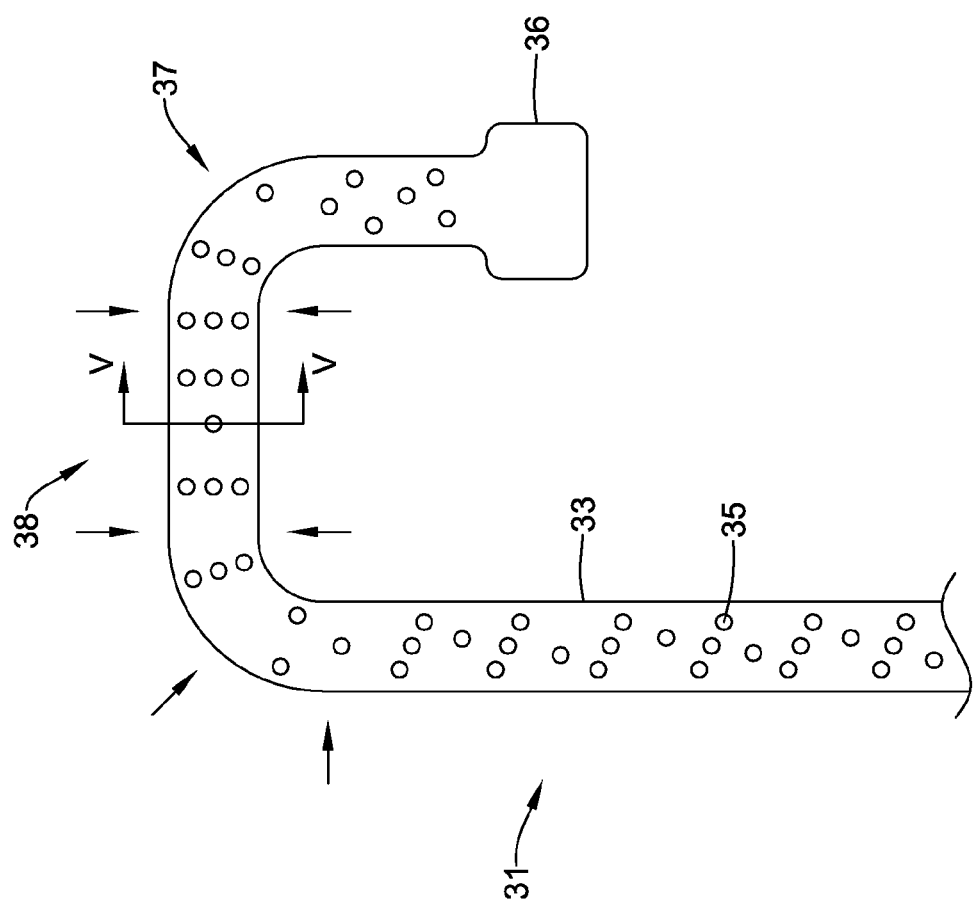
FIG. 3 is a side view of a steering guide catheter in accord with another alternative embodiment of the present invention.

FIG. 3 is a side view of a steering guide catheter that may be employed in an alternative embodiment of the present invention. Visible in FIG. 3 is a bendable curved memory portion 38 of the steering guide catheter 31, a distal tip 36, the catheter wall 33, and flushing orifices 35. Also labeled in FIG. 3 are ultraviolet rays 37, which may be used to create some cross-linking of the bendable curved memory portion 38 of the steering guide catheter 31.

Figure 7:
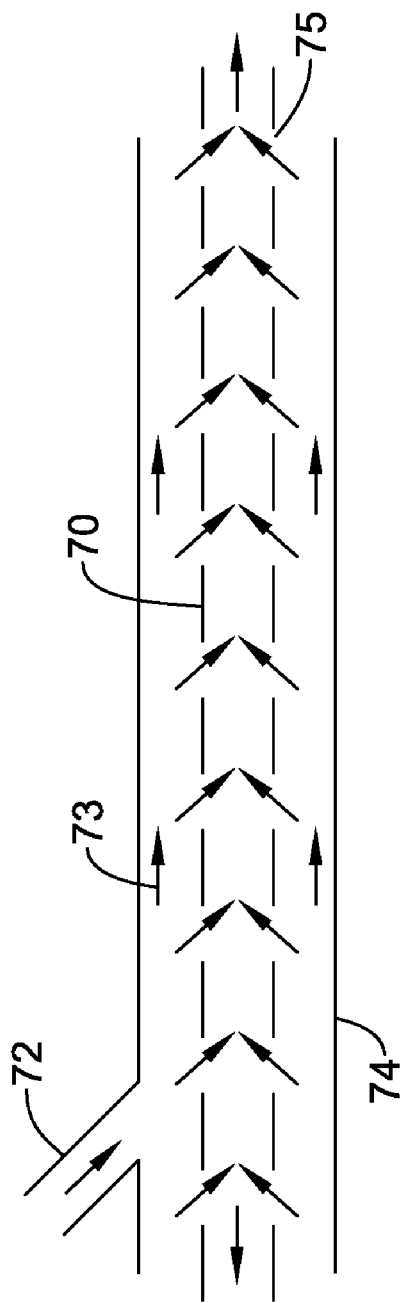
FIG. 7 is a side view of a guide-in-guide catheter system in accord with another alternative embodiment of the present invention.

As shown in FIG. 7, the steering guide catheter 31 may be inserted into an outer catheter during the performance of a medical procedure. In certain situations it is preferable to have the steering guide catheter 31 pre-shaped into a form that will more easily provide access to the target area sought to be worked on.

In this embodiment, the pre-forming is completed by exposing a portion of the steering guide catheter to ultraviolet lights such that the material that the steering guide 31 is composed of will begin to crosslink and will begin to accept the predetermined shape. The predetermined shape, in this instance a 'U', may be determined based on clinical trials. In other words, the exact dimension length, turning radii, and other criteria can be determined and imposed on the steering guide catheter well before the performance of the medical procedure using it.

The bendable curved memory portion 38 of the steering guide catheter 31 may be made from numerous materials that are capable of being pre-configured, including polyetherester block polymer and polytetrafluoroethylene (PTFE). In use, this bendable curved memory portion 38 will be temporarily straightened as it is urged through the straighter portions of an LVS catheter. Then, upon emerging from the distal end of the LVS catheter, the bendable curved memory portion 38 may return to its bended configuration, or to substantially its previous bended configuration, in either case so that ready access may be provided to a target site. Once the steering guide catheter 38 is properly positioned, an injection catheter or some other type of working tool may be snaked through the steering guide catheter 31, emerging from its distal tip 36, so that a medical procedure may be performed. Other memory materials that may be employed in the bendable portion include nitinol, which would return back to its original configuration upon being exposed to the heat of the body. This crosslink system can be applied to any catheter curve including those in the outer and middle catheters.

Figure 4:
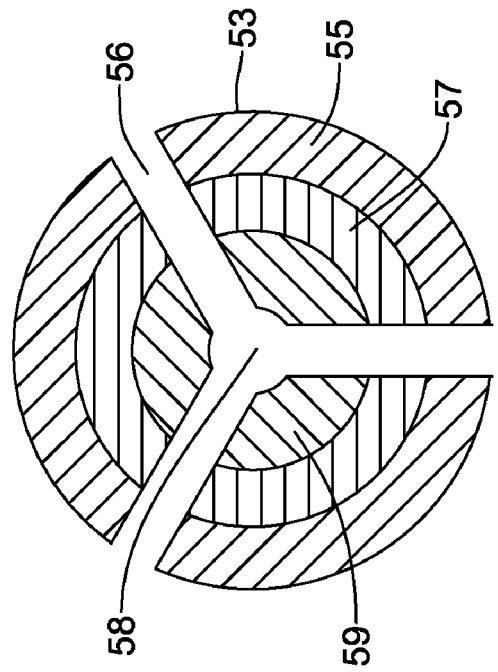
FIG. 4 is a cross-sectional view taken along line V-V of FIG. 3.

FIG. 4 is a cross-sectional view taken along line V-V of FIG. 3. As can be seen in FIG. 4, the steering guide catheter 31 contains a lubricious material 49, in this case a PTFE liner, a plurality of flushing orifices 35, an outer layer 45, a reinforcing member or structure 44, an inner layer 47, and a channel 48. The reinforcing member 44, in this embodiment a braid, may be used to help strengthen the steering guide catheter, it may also improve the kink resistance of the steering guide catheter 31. Comparatively, the lubricious material 49, in this case a PTFE liner, may be used to help facilitate the travel of another catheter within the channel 48 during the performance of a medical procedure.

In this particular embodiment, the inner layer 47 and the outer layer 45 are made from the same material. In alternative embodiments, and as discussed below, these layers may be made from different materials. Moreover, only a single layer of material may be employed in still other alternative embodiments.

The degree of cross-linking in the bendable curved memory portion 38 of the steering guide catheter 31 may be controlled by the degree of UV intensity and the exposure time. It may be dependent upon the required need for stiffness and curve retention.

Figure 5:
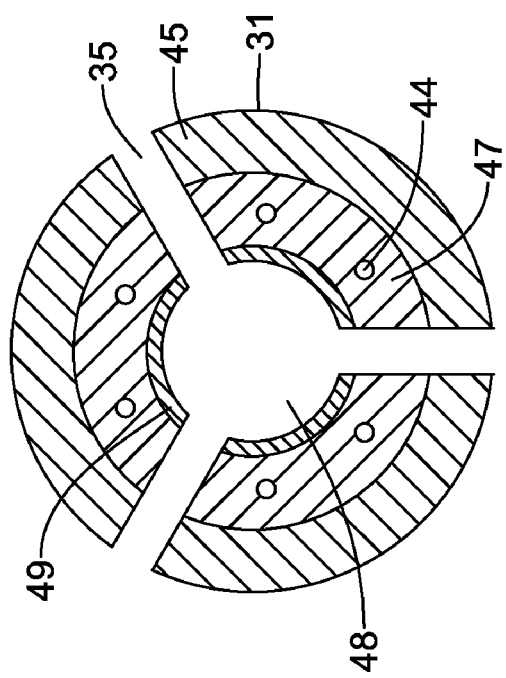
FIG. 5 is a cross-sectional view of a steering guide catheter in accord with another alternative embodiment of the present invention.

FIG. 5 is a cross-section of an alternative embodiment of the present invention. In FIG. 5, the steering guide catheter contains three layers: an inner layer 59, a middle layer 57, and an outer layer 55. The steering guide catheter also contains a channel 58 and a plurality of flushing orifices 56. In this embodiment the inner layer 59 may have the highest stiffness of the three layers, with the hardness ranging from between 64D to 82D. Comparatively, the outer layer 55 may have a hardness ranging from 30D to 67D. The middle layer 57 may have a hardness ranging from 30D to 67D as well. An advantage of placing the highest hardness in the center of the catheter is that by doing so the rigidity of the catheter can be increased without significantly affecting the catheter's ability to retain a curved configuration. In other words, by making the inner layer of the catheter the hardest, the catheter may be flexible enough to allow for its insertion down the lumen of the outside or surrounding catheter, but at the same time may retain its curved configuration such that once it emerges from the distal end of the outer catheter it will snap back substantially to its previously curved configuration. Then, as needed, the catheter may be further manipulated or steered during the medical procedure being performed to access the target site.

In this embodiment, as the hardness decreases as one moves from the inside of the catheter to the outside of the catheter the yield strain will preferably decrease as one moves from the outside layer, through the middle layer and into the inner layer of the catheter. Likewise, in other embodiments that also employ more layers, this same differential layering may be employed.

Figure 6:
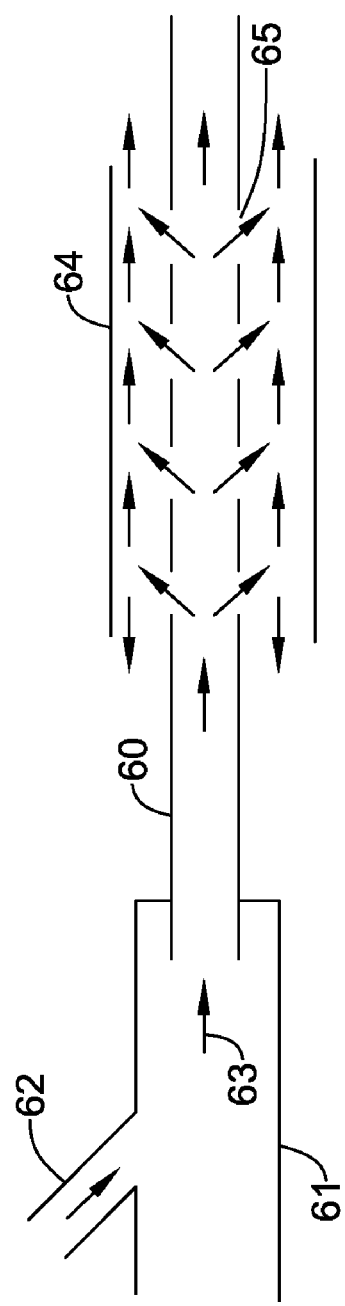
FIG. 6 is a side view of a guide-in-guide catheter system in accord with another alternative embodiment of the present invention.

FIG. 6 is a side view of an alternative embodiment of the present invention showing a flushing line 62 fluidly coupled to an inner catheter 60 having a plurality of flushing orifices 65. The flushing line 62 in this embodiment is fluidly coupled to the inner catheter 60 through the use of a flushing ring 61. As can be seen, by configuring the flushing line 62 and the inner and outer catheters 60 and 64 in this fashion, fluid moves through the flushing line 62, down the inner catheter 60 in the direction of arrows 63, and exits the inner catheter 60 through the flushing orifices 65 into the outer catheter 64. Consequently, through this configuration both the inner catheter 60 and the outer catheter 64 can be flushed by a single flushing line during the performance of a medical procedure. An advantage of this configuration is that it can eliminate the need for a second flushing line coupled directly to the outer catheter.

FIG. 7 is a side view of an inner and outer catheter in accordance with a preferred alternative embodiment of the present invention. In FIG. 7 a flushing line 72 is fluidly coupled to outer catheter 74. This outer catheter 74 contains an inner catheter 70 that has a plurality of flushing orifices 75. The direction of flushing fluid traveling in this system is depicted by arrows 73. As can be seen in the figure, flushing fluid traveling down the flushing line 72 enters the outer catheter 74 and then travels into the inner catheter 70 through the flushing orifices 75. Consequently, in this configuration, as with the above configuration, only a single flushing line may be required to flush both the inner and outer catheters in the system. In the embodiments of both FIG. 6 and FIG. 7, the outer catheter 64, 74 may be an LVS catheter while the inner catheter 60, 70 may be a steering guide catheter.

The therapeutic that may be deployed using the systems of the present invention can include numerous available therapeutics including pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22"), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic / anti-proliferative / anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; anti-microbials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability.

Polynucleotide sequences useful in practice of the invention include DNA or RNA sequences having a therapeutic effect after being taken up by a cell. Examples of therapeutic polynucleotides include anti-sense DNA and RNA; DNA coding for an antisense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Organs and tissues that may be treated by the methods of the present invention include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

The therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

While various embodiments have been described above, other embodiments of the present invention are also plausible. For example, while a single flushing line is shown supplying flushing fluid to the various embodiments presented above, two flushing lines may be used. Moreover, while no optical or sensory equipment has been described with any of these catheters, either optical and sensory equipment may be displaced through the catheters as required by the particular medical procedures being performed to assist the practitioner during the procedure.

What is claimed is:

1. A medical catheter system comprising:
   a first catheter having
      an entrance orifice,
      an exit orifice,
      a channel connecting the entrance orifice and the exit orifice,
      a wall surrounding the channel, the hardness of the wall surrounding the channel, when considered from an initial reference point at the entrance orifice and traveling towards the exit orifice, regardless of the orientation of the wall, decreasing in hardness in a first distinct region then increasing in hardness in a second distinct region and then decreasing in hardness again in a third distinct region, the hardness of the third region being different than the hardness of the first region and,
   a second catheter located within the first catheter, the first catheter sized to allow the second catheter to move within it, the second catheter having a steerable distal portion and a bendable curved memory portion;
   wherein the bendable curved memory portion of the second catheter contains a cross-linking polymer activated by ultra-violet light, and when activated the curved memory portion becomes shaped into a predetermined shape.

2. The medical catheter system of claim 1 further comprising:
   a third catheter located within the second catheter, the second catheter sized to allow the third catheter to move within it.

3. The medical catheter system of claim 1 wherein the bendable curve memory portion of the second catheter contains an outer layer with a first hardness and an inner layer with a second hardness, the second hardness being harder than the first hardness.

4. The medical catheter system of claim 1 wherein the second catheter has an outer layer with a first hardness and an inner layer with a second hardness, the second hardness being harder than the first hardness.

5. The medical catheter system of claim 1 wherein the second catheter has a plurality of flushing orifices.

6. The medical catheter system of claim 5 wherein the plurality of flushing orifices are in fluid communication with a flushing line coupled to the first catheter.

7. The medical catheter system of claim 1 further comprising a flushing line coupled to the first catheter.

* * * * *